(12) United States Patent
Tahara (10) Patent No.: US 9,212,984 B2
(45) Date of Patent: Dec. 15, 2015

(54) MICROPARTICLE ANALYSIS APPARATUS AND MICROPARTICLE ANALYSIS METHOD

(71) Applicant: Sony Corporation, Tokyo (JP)

(72) Inventor: Katsutoshi Tahara, Tokyo (JP)

(73) Assignee: Sony Corporation, Tokyo (JP)

( * ) Notice: Subject to any disclaimer, the term of this patent is extended or adjusted under 35 U.S.C. 154(b) by 9 days.

(21) Appl. No.: 14/026,023

(22) Filed: Sep. 13, 2013

(65) Prior Publication Data

US 2014/0087453 A1    Mar. 27, 2014

(30) Foreign Application Priority Data

Sep. 21, 2012  (JP) .................................. 2012-208319

(51) Int. Cl.
  *G01N 15/14* (2006.01)
  *G01N 15/10* (2006.01)
(52) U.S. Cl.
  CPC ........ *G01N 15/1434* (2013.01); *G01N 15/1429* (2013.01); *G01N 15/1459* (2013.01); *G01N 2015/1006* (2013.01)
(58) Field of Classification Search
  USPC .......... 356/335–343, 28, 28.5, 39; 422/82.09, 422/82.05, 82.08; 436/63, 164, 172
  See application file for complete search history.

(56) References Cited

U.S. PATENT DOCUMENTS

| 4,801,205 | A | * | 1/1989 | Tatsuno ........................ 356/336 |
| 5,296,910 | A | * | 3/1994 | Cole ............................ 356/28.5 |
| 5,492,833 | A | * | 2/1996 | Rodriguez et al. .............. 436/63 |
| 5,502,561 | A | * | 3/1996 | Hutchins et al. ............... 356/336 |
| 5,561,515 | A | * | 10/1996 | Hairston et al. ................ 356/28 |
| 2002/0141902 | A1 | * | 10/2002 | Ozasa et al. ................ 422/82.09 |
| 2008/0043219 | A1 | * | 2/2008 | Bivolaru et al. .............. 356/28.5 |
| 2008/0079929 | A1 | * | 4/2008 | Luo et al. ........................ 356/73 |
| 2010/0108910 | A1 | * | 5/2010 | Morrell et al. .............. 250/459.1 |
| 2010/0165325 | A1 | * | 7/2010 | Tabata ............................ 356/39 |

FOREIGN PATENT DOCUMENTS

| JP | 2012-026837 A | 2/2012 |
| JP | 2012-047464 A | 3/2012 |

* cited by examiner

*Primary Examiner* — Sang Nguyen
(74) *Attorney, Agent, or Firm* — Sony Corporation

(57) ABSTRACT

There is provided a microparticle analysis apparatus including a light detection unit configured to detect forward-scattered light generated from a microparticle that is an analysis target. The light detection unit includes a circuit having a high-pass filter that removes low frequency noise included in light entering the light detection unit and switches to the high-pass filter according to a predetermined frequency of the forward-scattered light.

9 Claims, 4 Drawing Sheets

MICROPARTICLE ANALYSIS APPARATUS AND MICROPARTICLE ANALYSIS METHOD

BACKGROUND

This present disclosure relates to a microparticle analysis apparatus and a microparticle analysis method. Specifically, it relates to a technique that can enhance the detection accuracy of forward-scattered light generated from microparticles.

In the related art, there has been used a microparticle analysis apparatus that irradiates light to a microparticle flowing in a flow cell or a channel formed in a microchip and detects the scattered light generated from the microparticle and the fluorescence generated from the microparticle or a fluorescent material labeled to the microparticle. This microparticle analysis apparatus measures the optical property of the microparticle that is an analysis object by detecting the scattered light and fluorescence generated from the microparticle and the like. Moreover, there has been used an apparatus (which may be referred to as "flow cytometer" or "cell sorter") adopting a fractionation-system configuration that sorts and recovers only microparticles having a given characteristic.

In the field of microparticle analysis apparatuses, various configurations have been suggested in order to improve the detection accuracy and analytical precision of the fluorescence and scattered light generated from a microparticle that is an analysis target. For example, JP 2012-26837A suggests a microparticle measurement apparatus having an optical filter including a transmission region of fluorescence and a transmission region of scattered light, on an optical path that guides the light generated from a microparticle to a light detector, in order to acquire backscattered light and fluorescence more efficiently. Moreover, JP 2012-47464A describes a microparticle measurement apparatus including a light focusing unit that focuses straight irradiated light without being scattered and scattering light scattered by a microparticle in a light receiving element divided into a plurality of regions, in order to enable a highly accurate measurement to be performed. This JP 2012-47464A suggests using an optical filter having a blocking region of irradiated light and a transmission region of scattered light, as a light focusing unit in the microparticle measurement apparatus.

SUMMARY

As described above, although various methods to improve the analytical precision has been suggested in the field of microparticle measurement apparatuses (microparticle analysis apparatus), it is desired to further improve the analytical precision with respect to the detection of forward-scattered light.

Therefore, in the present disclosure, it is a main purpose to provide a microparticle analysis apparatus that can improve the analytical precision with respect to the detection of forward-scattered light generated from a microparticle that is an analysis target.

The present inventors zealously conduct research in a repeated manner in order to improve the analytical precision (detection accuracy) with respect to the detection of forward-scattered light. In the research process, first, the present inventors ascertained that low frequency noise is unfortunately caused due to the mechanical vibration on the structure of a microparticle analysis apparatus. The low frequency noise due to the mechanical vibration is included in transmitted light without being irradiated by microparticles in light emitted from an optical source and the light enters a light detection unit that detects forward-scattered light. To be more specific, in the low frequency noise that enters the light detection unit to detect forward-scattered light, the diameter of a microparticle that is an analysis target is small, which causes the deterioration of the SN ratio as the signal output level of forward-scattered light is lower. Moreover, the present inventors found that, when the diameter of a microparticle that is an analysis target is small and the signal output level of forward-scattered light is low, the frequency of the forward-scattered light is high. Subsequently, they come up with an idea that it is possible to prevent the deterioration of the SN ratio by removing the low frequency noise at that time, S and found the present disclosure.

According to an embodiment of the present technology, there is provided a microparticle analysis apparatus including a light detection unit configured to detect forward-scattered light generated from a microparticle that is an analysis target. The light detection unit includes a circuit having a high-pass filter that removes low frequency noise included in light entering the light detection unit and switches to the high-pass filter according to a predetermined frequency of the forward-scattered light. By this configuration, even if the low frequency noise due to the mechanical vibration on the structure of an apparatus enters a light detection unit, it is possible to remove the low frequency noise in a high-pass filter. Subsequently, by switching to the high-pass filter according to a predetermined frequency of forward-scattered light, the light detection unit can remove the low frequency noise when there is a possibility that the SN ratio of detection by the light detection unit is deteriorated by the low frequency noise. Here, in the present disclosure, to "remove low frequency noise" includes not only the complete removal of the low frequency noise but also the removal of part of the low frequency noise and the reduction of the low frequency noise.

It is preferable that the light detection unit switches to the high-pass filter when the predetermined frequency is equal to or higher than 200 kHz.

It is preferable that the high-pass filter removes low frequency noise included in leakage light which avoids a zero-order light removal unit arranged between the microparticle and the light detection unit and which enters into the light detection unit.

Further, it is preferable that the high-pass filter removes noise of a frequency lower than 2 kHz.

It is preferable that the circuit includes a channel directly connected from an input side to an output side and a channel having the high-pass filter. The channel directly connected and the channel having the high-pass filter are connected in parallel. It is preferable that the circuit includes a switch element to perform switching to one of the channel directly connected and the channel having the high-pass filter.

Further, it is preferable that the circuit includes an amplifier configured to amplify a detection signal of the forward-scattered light.

In addition, according to an embodiment of the present technology, there is provided a microparticle analysis method including removing low frequency noise included in light entering a light detection unit in a circuit having a high-pass filter according to a predetermined frequency of forward-scattered light generated from a microparticle that is an analysis target to analyze the microparticle.

In an embodiment of the present technology, the term "microparticle" has a broad meaning that includes biologically-relevant microparticles such as cells, microbes, ribosomes and the like, as well as synthetic particles such as latex particles, gel particles, industrial particles and the like.

Examples of biologically-relevant microparticles include the chromosomes, liposomes, mitochondria, organelles (cell organelles) that form various cells. Examples of cells include animal cells (hematopoietic cells etc.) and plant cells. Examples of microbes include bacteria such as *E. coli*, viruses such as tobacco mosaic virus, fungi such as yeast and the like. Further example of biologically-relevant microparticles includes nucleic acids, proteins, complexes of these and the like. Examples of industrial particles include organic or inorganic polymer materials, metals and the like. Examples of organic polymer materials include polystyrene, styrene-divinyl benzene, poly methyl methacrylate and the like. Examples of inorganic polymer materials include glass, silica, magnetic materials and the like. Examples of metals include metal colloids, aluminum and the like. Examples of inorganic polymer materials include glass, silica, magnetic materials and the like. Examples of metals include metal colloids, aluminum and the like. Although the shape of these microparticles is usually spherical, the microparticles may also have a non-spherical shape. Further, the size and mass of these microparticles is not especially limited.

The present disclosure provides a microparticle analysis apparatus and microparticle analysis method that can improve the analytical precision with respect to the detection of forward-scattered light generated from a microparticle that is an analysis target.

DETAILED DESCRIPTION OF THE EMBODIMENT(S)

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

In the following, a preferred embodiment of the present disclosure is described with reference to the drawings. Here, the embodiment described below shows an example of a representative embodiment of the present disclosure and the range of the present disclosure is not interpreted narrowly by this. An explanation is given in the following order.
1. Configuration of microparticle analysis apparatus
2. Operation of microparticle analysis apparatus
<1. Configuration of Microparticle Analysis Apparatus>

Figure 1:
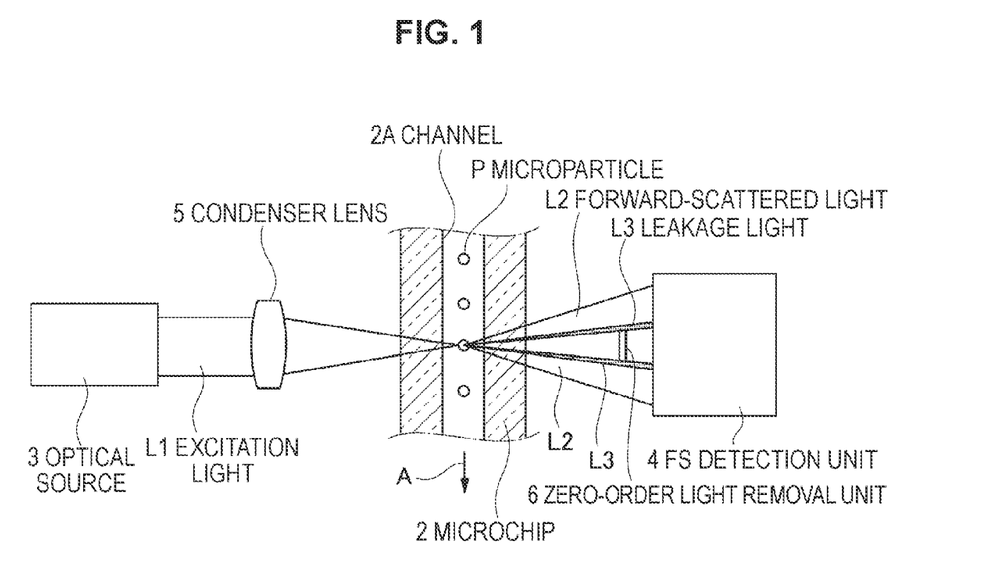
FIG. 1 is a pattern diagram to describe a configuration of an optical detection system example in a microparticle analysis apparatus according to an embodiment of the present disclosure.

The microparticle analysis apparatus according to the embodiment of the present disclosure includes a channel system such as a flow cell and a microchip, and an optical detection system that detects optical elements such as fluorescence (FL), forward-scattered light (FS) and backscattered light (BS) generated from a microparticle passing through a channel of the channel system. FIG. 1 is a pattern diagram to describe a schematic configuration of a forward-scattered light detection system (which may be referred to as "FS detection system" below) in an optical recognition system of a microparticle analysis apparatus 1 according to the embodiment of the present disclosure.

The channel system of the microparticle analysis apparatus according to the present embodiment includes a channel 2a formed in a microchip 2. In the channel 2a formed in the microchip 2, a sample liquid and a microparticle (sample) P that is a sample target included in the sample liquid are flowed. Since the microchip 2 is suitable for a disposable use (disposable), the use of the channel 2a formed in the microchip 2 is preferable in that the cross contamination between measurements (i.e., between samples) is easily prevented. For example, the microchip 2 includes a substrate formed with various resin materials such as glass, PC, PMMA, PE, PP, PS and polydimethylsiloxane (PDMS). For example, the channel 2a can be formed to the substrate by the etching, injection molding, nanoimprint and machine processing. Here, the channel may include a flow cell formed in the substantially prismatic shape or substantially cylinder shape made of crystal, quartz or ceramic.

As illustrated in FIG. 1, the FS detection system of the microparticle analysis apparatus 1 according to the embodiment of the present disclosure includes an optical source 3 and a light detection unit 4 that detects forward-scattered light L2 generated from microparticle P to which light L1 from the optical source 3 is irradiated. Since this the light detection unit 4 detects forward-scattered light L2, it is referred to as "forward-scattered light detection unit 4" (which may be referred to as "FS detection unit 4" below). Moreover, the present embodiment exemplifies a configuration including a condenser lens 5 that forms light L1 from the optical source 3 in the channel 2a (microparticle P) on an optical path between the optical source 3 and the channel 2a (microparticle P). In addition, the present embodiment exemplifies a configuration in which the FS detection system includes a zero-order light removal unit 6 on an optical path between the channel 2a (microparticle P) and the FS detection unit 4 in the present embodiment.

The optical source 3 can emit excitation light, and irradiates light (i.e., excitation light) to microparticle P in a sample liquid passing through the channel 2a. As the optical source 3 a laser diode (which may be referred to as "LD" below) is suitably used. In addition to the LD, a SHG (Second Harmonic Generation) laser, a solid state laser, a gas laser and a high brightness LED (Light Emitting Diode) may be used as an optical source. Moreover, as the optical source 3, a plurality of lights with different wavelengths may be used.

Light L1 (i.e., excitation light) emitted from the optical source 3 is irradiated to microparticle P flowing in the channel 2a in the direction of arrow A in FIG. 1 through the condenser lens 5. At this time, fluorescence and demanded scattered light such as forward-scattered light L2 and backscattered light are emitted from microparticle P. Here, the fluorescence and the demanded scattered-light elements are important optical elements to acquire optical information (i.e., characteristics) of microparticle P. The size or shape of a cell that is an analysis target may be chiefly analyzed from forward-scattered light L1 among the optical elements.

The FS detection unit 4 detects forward-scattered light L2 generated from microparticle P to which excitation light L1 is irradiated. Forward-scattered light L2 is the light scattered from microparticle P to which excitation light L1 is irradiated generally at an angle of about 1 to 19 degrees with respect to the optical axis of light L1 from the optical source 3, and chiefly acquires information on the size of a microparticle (e.g., cell). For example, the FS detection unit 4 includes a light detector such as a photodiode (PD). Moreover, when forward-scattered light L2 generated from microparticle P is incident, the FS detection unit 4 converts forward-scattered light L2 into an electric signal (i.e., voltage pulse).

The zero-order light removal unit 6 arranged between the channel 2a (microparticle P) and the FS detection unit 4 causes light L1 emitted from the optical source 3 to be permeable without being irradiated to microparticle P and blocks light (i.e., zero-order light) that enters the FS detection unit 4. This zero-order light removal unit 6 is arranged in the center of the optical axis of light L emitted from the optical source 3 on the optical path between the channel 2a (microparticle P) and the FS detection unit 4. The zero-order light removal unit 6 only has to include a member that can block light of a wavelength according to the wavelength of light L1 emitted from the optical source 3, and, for example, includes a light-shielding film, a gobo and an optical mask, and so on.

Even by the zero-order light removal unit 6, it is not possible to completely remove light L1 from the optical source 3, which penetrates without being irradiated to microparticle P, and there is a case where partial light of this light L1 enters the FS detection unit 4 as leakage light L3.

Figure 2:
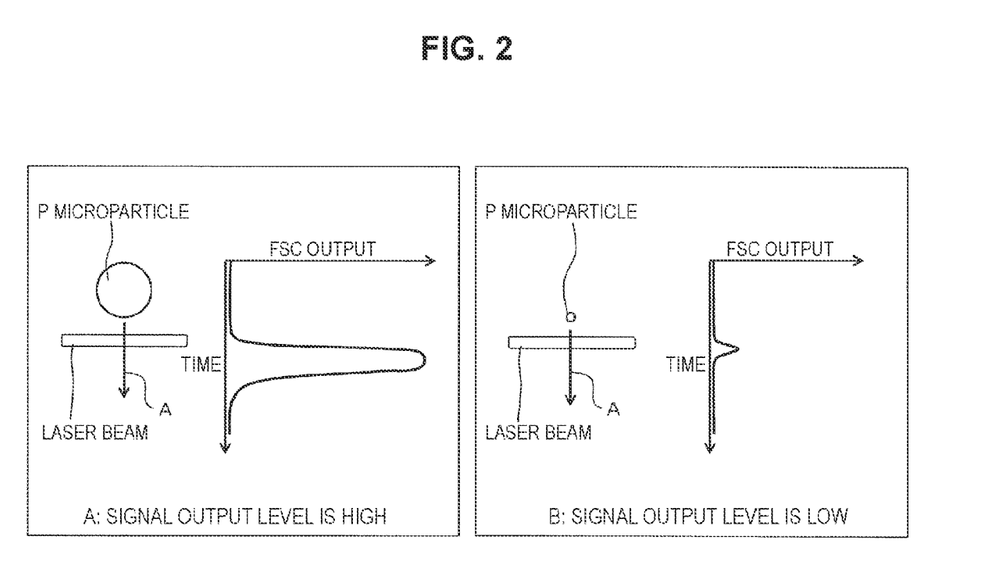
FIG. 2 is a pattern diagram to describe the signal level of forward-scattered light detected when a microparticle that is an analysis target passes the laser beam in a microparticle analysis apparatus according to an embodiment of the present disclosure.

Leakage light L3 entering the FS detection unit 4 may include the low frequency noise caused due to the mechanical vibration on an apparatus structure. Since this leakage light L3 directly enters the FS detection unit 4, when leakage light L3 is large with respect to forward-scattered light L2, it is likely to lead to the deterioration of the SN ratio of the FS detection system. That is, when the diameter of microparticle P that is an analysis target is small and the signal output level of forward-scattered light L2 is low (see FIG. 2B), leakage light L3 is relatively large with respect to forward-scattered light L2 and the SN ratio of the FS detection system may deteriorate. Here, FIG. 2 FIG. 2 is a diagram typically illustrating the signal output level of forward-scattered light L2 detected when microparticle P passes through a laser beam from the optical source (LD). FIG. 2A illustrates a state where the diameter of microparticle P is large and the signal output level is high, and FIG. 2B illustrates a state where the diameter of microparticle P is small and the signal output level is low.

The present inventors have focused attention on that the diameter of microparticle P that is an analysis target is small and close to the limitation of the analysis ability of the apparatus, and, when the signal output level of forward-scattered light L2 generated from microparticle P is low (see FIG. 2B), the frequency of this forward-scattered light L2 is high. Therefore, regarding the deterioration of the SN ratio, as described later, it is assumed that the FS detection unit 4 includes a high-pass filter that switches according to the frequency of forward-scattered light L2. Here, generally, regarding the analysis ability of the microparticle analysis apparatus, the diameter of the microparticle that is the analysis target is in the range of 0.5 μm to 40 μm, but, in a microparticle analysis apparatus in the related art, the detection accuracy of forward-scattered light is low when the diameter of the microparticle is small and less than 2 μm, for example. The microparticle analysis apparatus according to present embodiment enables forward-scattered light L2 to be accurately detected even in a case where the diameter of microparticle P is small and close to the limitation of the analysis ability of the apparatus.

Figure 3:
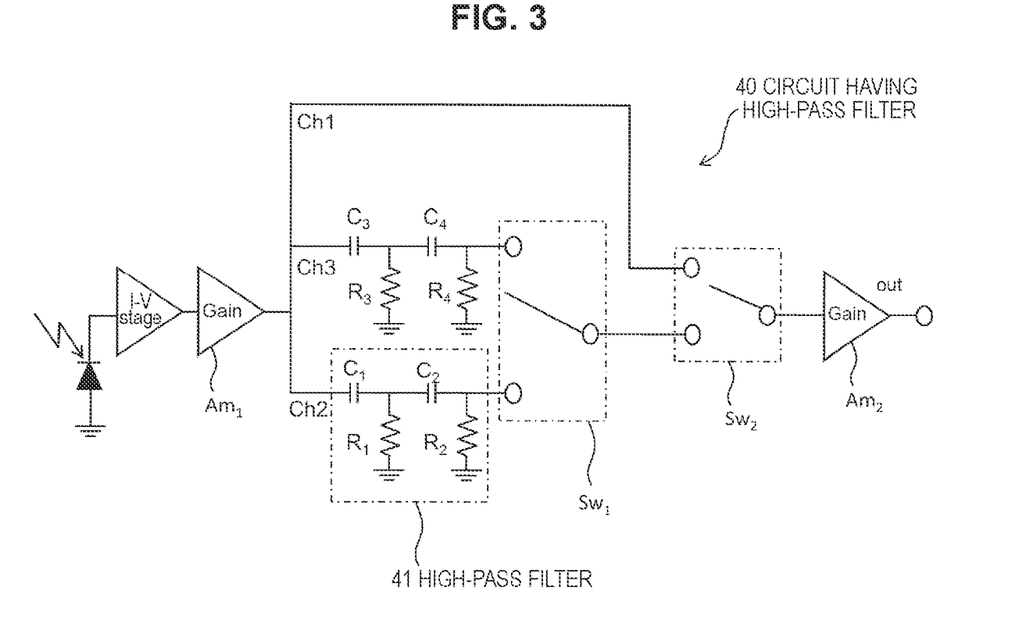
FIG. 3 is a diagram indicating an example of a circuit included in a light detection unit in a microparticle analysis apparatus according to an embodiment of the present disclosure.

For example, the FS detection unit 4 includes a circuit 40 having a high-pass filter 41 that removes the low frequency noise as illustrated in FIG. 3, and adopts a configuration that switches to the high-pass filter 41 according to a predetermined frequency of forward-scattered light L2. To be more specific, it is suitable that the FS detection unit 4 switches to the high-pass filter 41 preferably when the frequency of forward-scattered light L2 is equal to or higher than 200 kHz, more preferably when the frequency of forward-scattered light L2 is equal to or higher than 250 kHz, and much more preferably when the frequency of forward-scattered light L2 is equal to or higher than 300 kHz. This is because, in a case where the frequency of forward-scattered light L2 is equal to or higher than 200 kHz, since the diameter of microparticle P that is an analysis target is small and the signal output level of forward-scattered light L2 is low, the SN ratio may deteriorate when the low frequency noise exists. From the viewpoint of this SN ratio improvement, the upper limit value of the frequency of forward-scattered light L2 at the time of switching to the high-pass filter 41 is not specifically limited. However, for example, the upper limit value may be set to be equal to or lower than 3 MHz in consideration of a case where the frequency of forward-scattered light L2 generated from microparticle P is the highest.

As described above, there is leakage light L3 which avoids the zero-order light removal unit 6 arranged between the channel 2a (i.e., microparticle P) and the FS detection unit (i.e., light detection unit) 4 and which enters the FS detection unit 4. Subsequently, this leakage light L3 includes the low frequency noise caused due to the mechanical vibration on the structure of the microparticle analysis apparatus 1. The microparticle analysis apparatus 1 according to the present embodiment can remove the low frequency noise included in leakage light L3 in the high-pass filter 41 held in the FS detection unit 4.

The frequency of the low frequency noise due to the mechanical vibration is up to, for example, several kHz (around 2 kHz). Moreover, when the frequency which the high-pass filter 41 removes is too large, an influence may be given to the waveform of forward-scattered light L2. From the viewpoint of a frequency band (several kHz) of the low frequency noise due to the mechanical vibration and influence on the detection waveform of forward-scattered light L2 that should be detected, it is suitable that the high-pass filter 41 removes the noise of frequency or less than 2 kHz.

From the viewpoint of frequency characteristics of the high-pass filter 41, it is suitable to set the constant of the circuit according to the attenuation rate requested for noise after taking into account the ratio between the generated low frequency noise and the signal output level. For example, the attenuation rate in a frequency of 200 Hz of the high-pass filter 41 is set to be preferably equal to or lower than −12 dB, more preferably equal to or lower than −15 dB, and much more preferably equal to or lower than −18 dB. Here, since the high-pass filter 41 has a characteristic of not passing (or of attenuating) a frequency lower than a cutoff frequency, the lower limit value of a frequency removed (or blocked) by the high-pass filter 41 is not limited.

As illustrated in FIG. 3 showing an example of the circuit 40 having the high-pass filter 41, the circuit 40 in the FS detection unit 4 includes first channel Ch1 of a path directly connected from the input side to the output side and second channel Ch2 having the high-pass filter 41. Further, first channel Ch1 and second channel Ch2 are connected in parallel. Moreover, in the circuit 40, third channel Ch 3 is installed which can support a case where it is the path directly connected from the input side to the output side and a case where it functions as a high-pass filter by changing the constant of a resistor or capacitor. This third channel Ch3 is installed in first channel Ch1 and second channel Ch2 in parallel.

In a case where the frequency of forward-scattered light L2 generated from microparticle P that is an analysis target is low and the signal output level of forward-scattered light L2 is much higher in which the SN ratio does not deteriorate even if above-mentioned leakage light L3 includes the low frequency noise, directly-connected first channel Ch1 is selected. To be more specific, as described above, it is suitable to perform setting such that first channel Ch1 is selected preferably when the frequency of forward-scattered light L2 is lower than 60 kHz, more preferably when the frequency of forward-scattered light L2 is lower than 80 kHz, and much more preferably when the frequency of forward-scattered light L2 is lower than 100 kHz.

Meanwhile, in a case where the frequency of forward-scattered light L2 generated from microparticle P is high and the signal output level of forward-scattered light L2 is much lower in which the SN ratio deteriorates when above-mentioned leakage light L3 includes the low frequency noise, second channel Ch2 (i.e., high-pass filter 41) is selected. To be more specific, as described above, it is suitable to perform setting such that second channel Ch2 is selected preferably when the frequency of forward-scattered light L2 is equal to or higher than 200 kHz, more preferably when the frequency of forward-scattered light L2 is equal to or higher than 250 kHz, and much more preferably when the frequency of forward-scattered light L2 is equal to or higher than 300 kHz.

In a case where the frequency of forward-scattered light L2 generated from microparticle P that is an analysis target is equal to or higher than the setting value of first channel Ch1 and lower than the setting value of second channel Ch2, third channel Ch3 is selected. To be more specific, it is suitable to perform setting such that third channel Ch3 is selected preferably when the frequency of forward-scattered light L2 is equal to or higher than 60 kHz and lower than 200 kHz, more preferably when the frequency of forward-scattered light L2 is equal to or higher than 80 kHz and lower than 250 kHz, and much more preferably when the frequency of forward-scattered light L2 is equal to or higher than 100 kHz and lower than 300 kHz. Moreover, it is possible to set third channel Ch3 to state (N.M) in which a resistor and a capacitor are not mounted, and it can be configured such that the user adequately sets (or replaces) the constants of the resistor and condenser to provide the function of the high-pass filter.

As illustrated in FIG. 3, in the present embodiment, the high-pass filter 41 includes two capacitors C1 and C2 which are tandem to an input signal, and two resistors R1 and R2 which are parallel to an input signal. In a case where the resistance values of the resistors in the high-pass filter 41 are r [Ω] and the capacitance values of the capacitors are c [F], cutoff frequency f [Hz] is expressed as following Equation (1).

$$f = 1/2\pi rc \qquad \text{(Equation 1)}$$

In a case where the high-pass filter 41 has a plurality of resistors and capacitors like the present embodiment, "r" and "c" shown in above-mentioned Equation (1) indicate combined resistance value r and combined capacitance value c. Here, the "combined resistance value" denotes a resistance value in a case where a plurality of resistances are replaced with one equivalent resistance in the high-pass filter 41. Moreover, the "combined capacitance value" denotes a capacitance value in a case where a plurality of capacitors are replaced with one equivalent capacitor in the high-pass filter 41.

It is suitable to provide a capacitor including a resistor having appropriate resistance r and a resistor having appropriate capacitance value c, such that a frequency (i.e., cutoff frequency f) removed (or blocked) by the high-pass filter 41 has the above-mentioned preferable numerical value. Here, the numbers of resistors and capacitors in the high-pass filter 41 are not specifically limited. Moreover, other elements except for the resistors and the capacitors may be installed in the high-pass filter 41.

For example, switching between channels Ch1 to Ch-3 in the circuit 40 having the above-mentioned high-pass filter 41 can be performed by a switch element. In the present embodiment, switch element Sw1 that enables switching between second channel Ch2 and third channel Ch3 is installed in the above-mentioned circuit 40. Moreover, switch element Sw2 that enables switching between first channel Ch1 and one of second channel Ch2 and third channel Ch3 is installed in the above-mentioned circuit 40. In the above-mentioned circuit 40, switching to each of channels Ch1, Ch2 and Ch3 selected according to a frequency of above-mentioned forward-scattered light L2 is performed by switch elements Sw1 and Sw2.

The circuit 40 having the high-pass filter 41 may include an amplifier that amplifies a detection signal of above-mentioned forward-scattered light L2. In the present embodiment, as illustrated in FIG. 3, the circuit 40 having the high-pass filter 41 includes two amplifiers Am1 and Am2.

In the present embodiment, in a case where directly-connected first channel Ch1 is selected according to the frequency of above-mentioned forward-scattered light L2, first channel Ch1 and amplifier Am2 are connected by switch element Sw2. The detection signal of forward-scattered light L2 passing through first channel Ch1 may be amplified by a predetermined gain in amplifier Am2. At this time, since the signal level of forward-scattered light L2 is high, it is suitable to set the gain of amplifier Am2 in a case where first channel Ch1 is selected, to be smaller than the gain of amplifier Am2 in a case where second channel Ch2 is selected.

Also, in the present embodiment, in a case where second channel Ch2 of the high-pass filter 41 is selected according to the frequency of above-mentioned forward-scattered light L2, second channel Ch2 and amplifier Am2 are connected by switch elements Sw1 and Sw2. The detection signal of forward-scattered light L2 passing through second channel Ch2 may be amplified by a predetermined gain in amplifier Am2. At this time, since the signal level of forward-scattered light L2 is low, it is suitable to set the gain of amplifier Am2 in a case where second channel Ch2 is selected, to be larger than the gain of amplifier Am2 in a case where first channel Ch1 is selected. In a case where second channel Ch2 is selected, since the low frequency noise is removed by the high-pass filter 41, it is possible to amplify a small signal of forward-scattered light L2 by amplifier Am2 and enhance the detection accuracy without picking up less low frequency noise.

In addition, in the present embodiment, in a case where third channel Ch3 of the high-pass filter 41 is selected according to the frequency of above-mentioned forward-scattered light L2, 3rd channel Ch3 and amplifier Am2 are connected by switch elements Sw1 and Sw2. The detection signal of forward-scattered light L2 passing through third channel Ch3 may be amplified by a predetermined gain in amplifier Am2. It is suitable to set the gain of amplifier Am2 in a case where third channel Ch3 is selected, between the gain in a case where first channel Ch1 is selected and the gain in a case where second channel Ch2 is selected.

Figure 4:
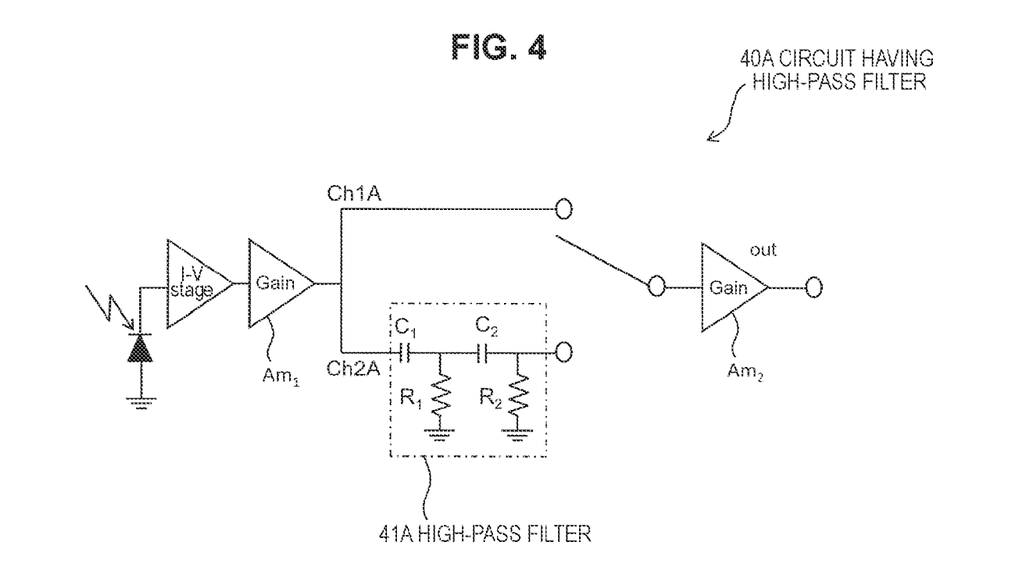
FIG. 4 is a diagram indicating another example of a circuit included in a light detection unit in a microparticle analysis apparatus according to an embodiment of the present disclosure.

In the circuit 40 according to the present embodiment illustrated in FIG. 3, it is suitable that switching of the gain of amplifier Am1 and switching between first to third channels (Ch1 to Ch3) are operated together. By operating switching in amplifier Am1 and switching between first to third channels (Ch1 to Ch3) together, it is possible to share a control signal. Moreover, in this case, it is suitable that amplifier Am1 is designed to have three-staged gains. Here, the circuit 40 having the high-pass filter 41 included in the FS detection unit 4 may include two channels. For example, as illustrated in FIG. 4, there may be provided the circuit 40A including directly-connected channel Ch1A and second channel Ch2A having the high-pass filter 41A that removes the low frequency noise, where these channels are mutually provided in parallel. In the circuit 40A, the number of channels is small, that is, two, and the circuit having the high-pass filter can be simplified.

For example, the microparticle analysis apparatus 1 can adopt the following configuration in addition to the FS detection system. The microparticle analysis apparatus according to the embodiment of the present disclosure may include a fluorescence detection system (FL detection system) that detects fluorescence (FL) and a backscattered light detection system (i.e., BS detection system) that detects backscattered light (BS). The FL detection system and the BS detection system may optionally include an optical lens, a dichroic mirror and an optical filter, and so on. The FL detection system includes a fluorescence detection unit (i.e., FL detection unit), and the FL detection unit detects fluorescence. The BS detection system includes a backscattered light detection unit (i.e., BS detection unit), and the BS detection unit detects backscattered light. For example, the FL detection unit and the BS detection unit include a photo-multiplier tube (PMT) and an area imaging element such as CCD and CMOS elements.

The microparticle analysis apparatus according to the embodiment of the present disclosure may adopt a configuration of a fractionation system that sorts and recovers a microparticle that is an analysis target, in addition to the above-mentioned configuration. The configuration of the fractionation system can be formed in the same way as a microparticle analysis apparatus in the related art. For example, the fractionation system includes: an electrically-charged unit that gives an electrical charge to a droplet including a microparticle discharged from a microchip; a pair of deflection plates faced and arranged so as to cover the droplet along the movement direction of the droplet; and a container that contains the droplet including the microparticle.

In addition to the above configuration, the microparticle analysis apparatus according to the embodiment of the present disclosure may include: a data analysis unit for optical property determination of microparticles; a tank unit that accumulates a sample liquid and the like; a control unit to control these components, as well as the microparticle analysis apparatus in the related art. The control unit may include a general-purpose computer having a CPU, memory and hard disk, and so on, and the hard disk contains an OS and a program that executes the microparticle analysis method (i.e., operation of the microparticle analysis apparatus) described later, and so on. For example, in the circuit 40 having the high-pass filter 41, the control unit can store and set the frequency of forward-scattered light L2 at the time when each of channels Ch1 to Ch3 is used. Moreover, switching between channels Ch1 to Ch3 (switching between switch elements Sw1 and Sw2) in the circuit 40 can be performed in the control unit.

Next, an operational effect of the microparticle analysis apparatus 1 according to the embodiment of the present embodiment is described. According to the microparticle analysis apparatus 1 of the present embodiment, by the configuration of the above-mentioned the FS detection unit 4, forward-scattered light L2 is detected in the high-pass filter 41 that removes the low frequency noise according to a predetermined frequency of forward-scattered light L2 generated from microparticle P. Therefore, even in a case where leakage light L3 including the low frequency noise due to the mechanical vibration on the apparatus structure enters the FS detection unit 4, it is possible to remove the low frequency noise in the high-pass filter 41. Therefore, it is possible to improve the SN ratio related to detection of forward-scattered light L2 and enhance the analytical precision. The existence of the low frequency noise deteriorates the SN ratio when the diameter of microparticle P is small and the signal output level of forward-scattered light L2 low (see FIG. 2B), that is, when the frequency of forward-scattered light L2 is high. Therefore, the microparticle analysis apparatus 1 of the present embodiment is configured such that the FS detection unit 4 switches to the high-pass filter 41 to detect forward-scattered light L2 when the frequency of forward-scattered light L2 is equal to or higher than 200 kHz. Therefore, it is possible to prevent the deterioration of the SN ratio due to the low frequency noise, enhance the detection accuracy of forward-scattered light L2 and improve the analytical precision.

<2. Operation of Microparticle Analysis Apparatus>

Next, an operation of the above-mentioned microparticle analysis apparatus 1 is described. First, light (i.e. excitation light) L1 from the optical source 3 is converged by the condenser lens 5 and irradiated to microparticle P flowing in the channel 2a. Moreover, part of light L1 emitted from the optical source 3 avoids the zero-order light removal unit 6 and enters the FS detection unit 4 as leakage light L3. Fluorescence and scattered-light elements (such as forward-scattered light L2 and backscattering) are emitted from microparticle P to which excitation light L1 is irradiated. At this time, forward-scattered light L2 generated from microparticle P enters the FS detection unit 4.

Forward-scattered light L2 entering the FS detection unit 4 is converted into an electric signal in the FS detection unit 4 and detected. At this time, the circuit 40 having the high-pass filter 41 that removes the low frequency noise, which is included in the FS detection unit 4, is used (see FIG. 3), and forward-scattered light L2 is detected in the high-pass filter 41 according to a predetermined frequency of forward-scattered light L2.

As the circuit 40 having the high-pass filter 41 included in the FS detection unit 4, as described above, for example, the circuit illustrated in FIG. 3 is used. In the case of the circuit 40 illustrated in FIG. 3, for example, forward-scattered light L2 is detected in second channel Ch2 having the high-pass filter preferably when the frequency of forward-scattered light L2 is equal to or higher than 200 kHz (more preferably when the frequency of forward-scattered light L2 is equal to or higher than 250 kHz, and much more preferably when the frequency of forward-scattered light L2 is equal to or higher than 300 kHz). Moreover, for example, forward-scattered light L2 is detected in directly-connected first channel Ch1 without the high-pass filter 41 preferably when the frequency of forward-scattered light L2 is lower than 60 kHz (more preferably when the frequency of forward-scattered light L2 is lower than 80 kHz, and much more preferably when the frequency of forward-scattered light L2 is lower than 100 kHz). Furthermore, forward-scattered light L2 is detected in third channel Ch3 preferably when the frequency of forward-scattered light L2 is equal to or higher than 60 kHz and lower than 200 kHz (more preferably when the frequency of forward-scattered light L2 is equal to or higher than 80 kHz and lower than 250 kHz, and much more preferably when the frequency of forward-scattered light L2 is equal to or higher than 100 kHz and lower than 300 kHz).

In a case where forward-scattered light L2 is detected in the high-pass filter 41 (i.e., second channel Ch2), the above-mentioned low frequency noise is removed by the high-pass filter 41. As a result, the SN ratio of detection of forward-scattered light L2 improves and the detection accuracy improves even when the signal level of forward-scattered light L2 is low. Moreover, the detection signal of forward-scattered light L2 passing through each of channels Ch1 to Ch3 is amplified in amplifier Am2. In a case where detection is performed in the high-pass filter, since the above-mentioned low frequency noise is removed, the low frequency noise is hardly picked up, a signal with low forward-scattered light L2 is amplified and the detection accuracy is further enhanced.

Here, it is possible to store the operation of the microparticle analysis apparatus according to the embodiment of the present disclosure in a hardware resource including the above-mentioned control unit and recording medium (such as a nonvolatile memory (e.g., USB thumb drive), HDD and CD), as a program, and realize it by the control unit.

Additionally, the present technology may also be configured as below.

(1) A microparticle analysis apparatus including:
a light detection unit configured to detect forward-scattered light generated from a microparticle that is an analysis target,
wherein the light detection unit includes a circuit having a high-pass filter that removes low frequency noise included in light entering the light detection unit and switches to the high-pass filter according to a predetermined frequency of the forward-scattered light.
(2) The microparticle analysis apparatus according to (1), wherein the light detection unit switches to the high-pass filter when the predetermined frequency is equal to or higher than 200 kHz.
(3) The microparticle analysis apparatus according to (1) or (2), wherein the high-pass filter removes low frequency noise included in leakage light which avoids a zero-order light removal unit arranged between the microparticle and the light detection unit and which enters into the light detection unit.
(4) The microparticle analysis apparatus according to any one of (1) to (3), wherein the high-pass filter removes noise of a frequency lower than 2 kHz.
(5) The microparticle analysis apparatus according to any one of (1) to (4),
wherein the circuit includes a channel directly connected from an input side to an output side and a channel having the high-pass filter, and
wherein the channel directly connected and the channel having the high-pass filter are connected in parallel.
(6) The microparticle analysis apparatus according to (5), wherein the circuit includes a switch element to perform switching to one of the channel directly connected and the channel having the high-pass filter.
(7) The microparticle analysis apparatus according to any one of (1) to (6), wherein the circuit includes an amplifier configured to amplify a detection signal of the forward-scattered light.
(8) A microparticle analysis method including:
removing low frequency noise included in light entering a light detection unit in a circuit having a high-pass filter according to a predetermined frequency of forward-scattered light generated from a microparticle that is an analysis target to analyze the microparticle.

EXAMPLE

The effects of the embodiment of the present disclosure are described according to the following example. The present example is a result of performing an effect confirmatory experiment of the embodiment of the present disclosure by the use of a flow cytometer (i.e., microparticle analysis apparatus) including the forward-scattered light detection system as illustrated in above-mentioned FIG. 1. Moreover, as a forward-scattered light detection unit in this flow cytometer, a photodiode is used in which a circuit including a high-pass filter that removes the low frequency noise is installed.

As a circuit having a high-pass filter included in the photodiode, the circuit as illustrated in above-mentioned FIG. 3 is used. Regarding the circuit used in the present example, in FIG. 3, it is designed such that the resistance values of resistors corresponding to resistors R1 and R2 are set to 2.2 kΩ and 4.7 kΩ respectively and the capacitance values of capacitors corresponding to capacitors C1 and C2 are set to 0.1 µF. Moreover, cutoff frequency f (frequency at −3 dB) of the high-pass filter in the circuit is 1.23 kHz and the attenuation rate in 200 Hz is −19 dB.

An LED and pulse generator that emit light of 600 nm are used as an optical source, an optical waveform (i.e., sine wave of 125 kHz subjected to half-wave rectification with 4µ second width) caused when the particle diameter of 3.0 µm is scattered taking into account the margin is created and enters the photodiode.

Figure 5:
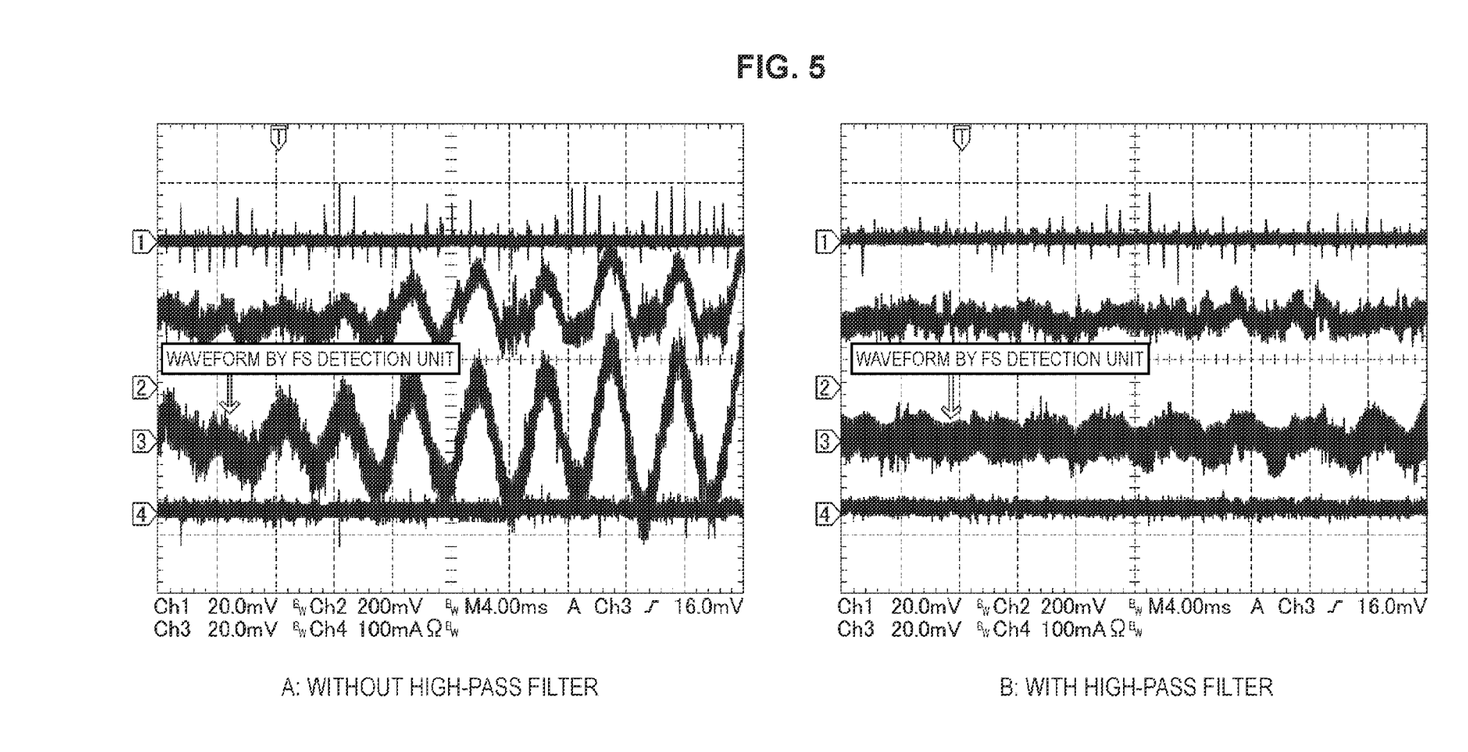
FIG. 5 is a diagram illustrating a demonstration result according to an embodiment to confirm an effect of a microparticle analysis apparatus according to the embodiment of the present disclosure.

The forward-scattered light generated from microbeads is detected in directly-connected first channel (Ch1) without the high-pass filter and second channel (Ch2) having the high-pass filter (see FIG. 3). FIG. 5 illustrates these demonstration results. As illustrated in FIG. 5, in the detection in the first channel, it is found that the noise is large (see FIG. 5A). By contrast with this, in the detection in the high-pass filter (i.e., the second channel), it is found that the noise is greatly reduced (see FIG. 5B).

Figure 6:
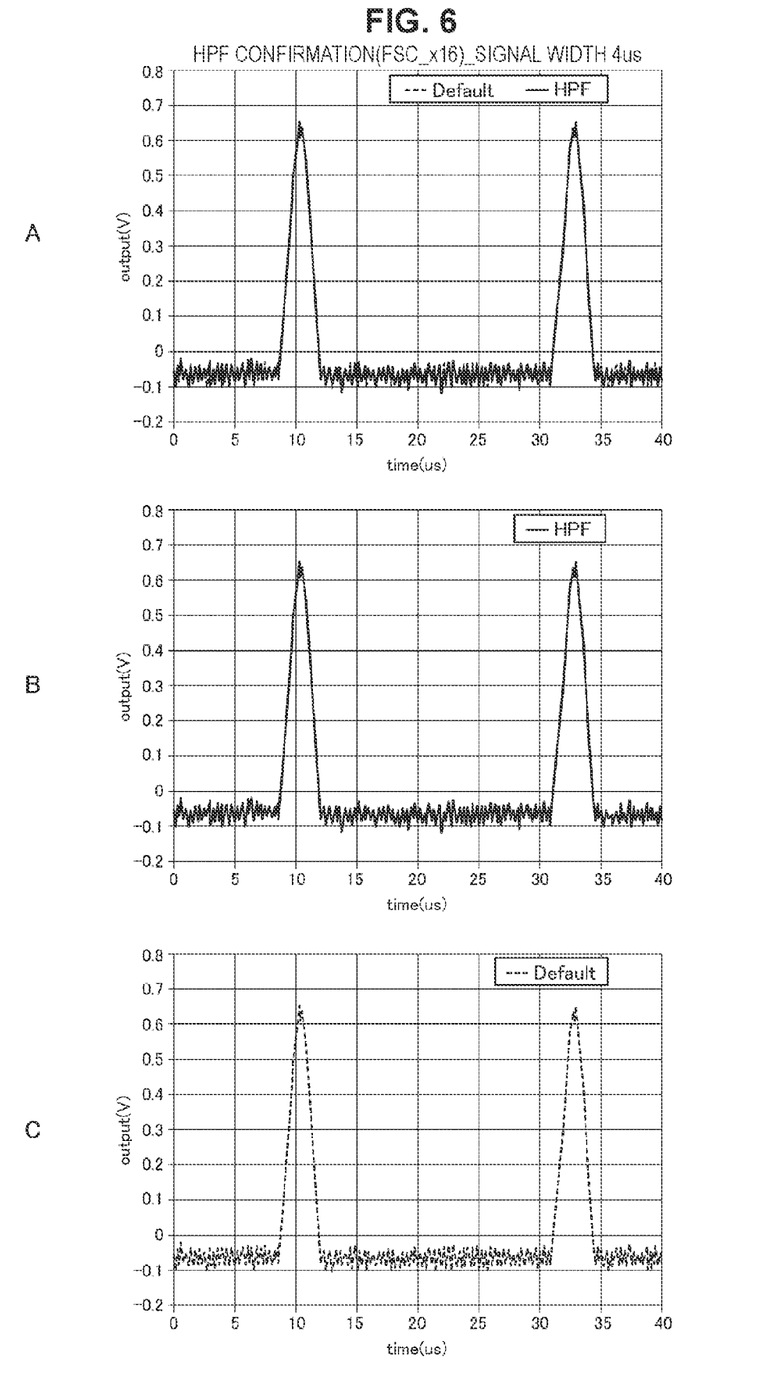
FIG. 6 is a diagram illustrating signal data of forward-scattered light detected by a light detection unit in an example to confirm the effect of a microparticle analysis apparatus according to the embodiment of the present disclosure.

Moreover, waveforms of forward-scattered light detected in the first channel and the high-pass filter (i.e., second channel) are illustrated in FIG. 6 respectively. FIG. 6A illustrates the waveforms of the forward-scattered light detected in the first channel and the high-pass filter (i.e., second channel) together. Also, FIG. 6B illustrates the waveform of the forward-scattered light detected in the high-pass filter (i.e., second channel) and FIG. 6 C illustrates the waveform of the forward-scattered light detected in the first channel. As illustrated in FIG. 6A, it is found that the waveform ("Default" in FIG. 6C) in the first channel without the high-pass filter and the waveform ("HPF" in FIG. 6B) in the second channel having the high-pass filter are matched and there is no distortion between both waveforms.

In view of the above, with respect to microparticle of 3.0 µm, it is found that it is possible to remove the low frequency noise without affecting the detection waveform of forward-scattered light that should be detected. Therefore, according to the microparticle analysis apparatus of the embodiment of the present disclosure, even in a case where the diameter of a microparticle is small and the signal output of forward-scattered light is low, it is possible to improve the SN ratio and enhance the detection accuracy (i.e., analytical precision) of forward-scattered light.

It should be understood by those skilled in the art that various modifications, combinations, sub-combinations and alterations may occur depending on design requirements and other factors insofar as they are within the scope of the appended claims or the equivalents thereof.

The present disclosure contains subject matter related to that disclosed in Japanese Priority Patent Application JP 2012-208319 filed in the Japan Patent Office on Sep. 21, 2012, the entire content of which is hereby incorporated by reference.

What is claimed is:

1. A microparticle analysis apparatus comprising:
    a light detection unit configured to detect forward-scattered light generated from a microparticle that is an analysis target,
    wherein the light detection unit includes:
    a high-pass filter that removes low frequency noise included in the forward-scattered light entering the light detection unit; and
    a switching element, wherein the switching element is configured to selectively connect and disconnect the high-pass filter according to a predetermined frequency of the forward-scattered light.

2. The microparticle analysis apparatus according to claim 1, wherein the light detection unit selectively connects and disconnects the high-pass filter when the predetermined frequency is equal to or higher than 200 kHz.

3. The microparticle analysis apparatus according to claim 2, wherein the high-pass filter removes low frequency noise, included in leakage light, which avoids a zero-order light removal unit arranged between the microparticle and the light detection unit and which enters into the light detection unit.

4. The microparticle analysis apparatus according to claim 3, wherein the high-pass filter removes noise of a frequency lower than 2 kHz.

5. The microparticle analysis apparatus according to claim 4, further comprising
    a first channel directly connected from an input side to an output side and a second channel having the high-pass filter,
    wherein the first channel directly connected and the second channel having the high-pass filter are connected in parallel.

6. The microparticle analysis apparatus according to claim 5,
    wherein the switching element performs switching to selectively connect and disconnect one of the first channel directly connected and the second channel having the high-pass filter.

7. The microparticle analysis apparatus according to claim 6, further comprising
    an amplifier configured to amplify a detection signal of the forward-scattered light.

8. A microparticle analysis method comprising:
    removing low frequency noise included in light, entering a light detection unit, in a high-pass filter;
    switching, by a switching element, to selectively connect and disconnect the high-pass filter according to a predetermined frequency of forward-scattered light generated from a microparticle that is an analysis target to analyze the microparticle.

9. The microparticle analysis apparatus according to claim 1, wherein the high-pass filter is selectively connected when frequency of the forward-scattered light is greater than a first threshold and signal output level of the forward-scattered light is lesser than a second threshold.

* * * * *